United States Patent [19]

Whittamore

[11] Patent Number: 5,731,323
[45] Date of Patent: Mar. 24, 1998

[54] QUINUCLIDINE DERIVATIVES AS SQUALENE SYNTHASE INHIBITORS

[75] Inventor: Paul Robert Owen Whittamore, Macclesfield, United Kingdom

[73] Assignee: Zeneca Limited, London, England

[21] Appl. No.: 454,119

[22] PCT Filed: Dec. 21, 1993

[86] PCT No.: PCT/GB93/02617

§ 371 Date: Jun. 5, 1995

§ 102(e) Date: Jun. 5, 1995

[87] PCT Pub. No.: WO94/14805

PCT Pub. Date: Jul. 7, 1994

[30] Foreign Application Priority Data

Dec. 21, 1992 [GB] United Kingdom ............. 9226573

[51] Int. Cl.⁶ ............. A01N 43/90; C07D 453/02
[52] U.S. Cl. ............. 514/305; 514/241; 514/255; 514/256; 544/180; 544/238; 546/133; 546/134; 546/137
[58] Field of Search ............. 544/238, 300, 544/310, 316, 319, 320, 298, 322, 324, 327, 328, 331, 333, 405, 180; 546/133, 134, 137; 514/241, 255, 256, 305

[56] References Cited

U.S. PATENT DOCUMENTS

| | | | |
|---|---|---|---|
| 3,405,134 | 10/1968 | Judd | 546/137 |
| 3,534,053 | 10/1970 | Salley et al. | 546/133 |
| 3,586,694 | 6/1971 | Shen et al. | 548/309.4 |
| 3,655,675 | 4/1972 | Carabateas | 546/224 |
| 3,679,690 | 7/1972 | Carabateas | 546/309 |
| 3,725,410 | 4/1973 | Potoski et al. | 544/362 |
| 3,763,168 | 10/1973 | Carabateas | 546/133 |
| 3,792,053 | 2/1974 | Potoski et al. | 546/137 |
| 3,857,848 | 12/1974 | Mauvernay et al. | 546/133 |
| 4,038,402 | 7/1977 | Kaminka et al. | 514/305 |
| 4,599,344 | 7/1986 | Morgan | 514/305 |
| 4,985,560 | 1/1991 | Sabb et al. | 544/115 |
| 5,135,935 | 8/1992 | Alberts | 514/305 |
| 5,242,914 | 9/1993 | Kawamoto et al. | 514/210 |
| 5,286,864 | 2/1994 | Walther et al. | 546/137 |
| 5,354,750 | 10/1994 | Scheffler et al. | 514/248 |
| 5,385,912 | 1/1995 | Neuenschwande et al. | 514/305 |

FOREIGN PATENT DOCUMENTS

| | | |
|---|---|---|
| 7713/91 | 11/1991 | Australia . |
| 1014958 | 8/1977 | Canada . |
| 2042860 | 11/1991 | Canada . |
| 38564 | 10/1981 | European Pat. Off. . |
| 130555 | 1/1985 | European Pat. Off. . |
| 0 307 142 | 3/1989 | European Pat. Off. . |
| 306148 | 3/1989 | European Pat. Off. . |
| 0 316 718 | 5/1989 | European Pat. Off. . |
| 0 322 182 | 6/1989 | European Pat. Off. . |
| 0 328 200 | 8/1989 | European Pat. Off. . |
| 0 330 826 | 9/1989 | European Pat. Off. . |
| 0 337 637 | 10/1989 | European Pat. Off. . |
| 0 370 415 | 5/1990 | European Pat. Off. . |
| 0 412 797 | 2/1991 | European Pat. Off. . |
| 0 458 214 | 11/1991 | European Pat. Off. . |
| 456519 | 11/1991 | European Pat. Off. . |
| 458214 | 11/1991 | European Pat. Off. . |
| 0 497 415 | 8/1992 | European Pat. Off. . |
| 2 323 303 | 12/1973 | Germany . |
| 25 02 916 | 11/1975 | Germany . |
| 41 16 582 | 11/1991 | Germany . |
| 04208267 | 7/1992 | Japan . |
| 1 416 958 | 12/1975 | United Kingdom . |
| 2 169 292 | 7/1986 | United Kingdom . |
| 92-15579 | 9/1992 | WIPO . |
| 9215579 | 9/1992 | WIPO . |
| 93-13096 | 7/1993 | WIPO . |
| 93/15073 | 8/1993 | WIPO . |
| 93/16048 | 8/1993 | WIPO . |

OTHER PUBLICATIONS

Chikashita, H. et al, Bull. Chem. Soc. Jpn. 1988, 61(10), pp. 3637–3648.

Polivka, Z. et al, Collect. Czech. Chem. Commun. 1988, 53(8), 1806–1811.

Temple, C. et al, J. Med. Chem. 1968, 11(6), 1213–5.

Singh, T. et al, J. Med. Chem. 1969, 12, 524–526.

Bondarenko, V.A. et al, Khim. –Farm Zh. 1978, 12(11), 56–60.

(List continued on next page.)

*Primary Examiner*—C. Warren Ivy
*Assistant Examiner*—Garth M. Dahlen
*Attorney, Agent, or Firm*—Pillsbury Madison & Sutro LLP; Intellectual Property Group

[57] ABSTRACT

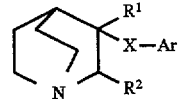

Compounds of formula (I) and their pharmaceutically acceptable salts in which $R^1$ is hydrogen or hydroxy; $R^2$ is hydrogen; or $R^1$ and $R^2$ are joined together so that $CR^1$—$CR^2$ is a double bond; X is selected from —$CH_2CH_2$—, —$CH=CH$—, —$C\equiv C$—, —$CH_2O$—, —$OCH_2$—, —$CH_2NH$—, —$NHCH_2$—, —$CH_2CO$—, —$COCH_2$—, —$N=CH$—, —$CH=N$—, —$CH_2S$— and —$SCH_2$— (wherein the sulphur atom in the latter two groups may optionally bear one or two oxygen atoms); Ar is a heterocyclic moiety containing up to three heteroatoms independently selected from nitrogen, oxygen and sulphur, and wherein Ar may optionally be unsubstituted or may bear one or more substituents independently selected from halogeno, hydroxy, amino, nitro, cyano, carboxy, carbamoyl, alkyl, alkenyl, alkynyl, alkoxy, alkylamino, di-alkylamino, N-alkylcarbamoyl, di-N,N-alkylcarbamoyl, alkoxycarbonyl, alkylthio, alkylsulphinyl, alkylsulphonyl, halogenoalkyl, alkanoylamino, ureido, N'-alkylureido, alkanoyl and oxime derivatives thereof and O-alkyl ethers of said oxime derivatives; are inhibitors of squalene synthase and hence useful in treating medical conditions in which a lowering of cholesterol is beneficial. Processes preparing these derivatives, pharmaceutical compositions containing them are also described together with their use in medecine.

14 Claims, No Drawings

OTHER PUBLICATIONS

Biniecki, S. et al, Acta. Pol. Pharm. 1982, 39(1–3), 1–7.

Kumazawa,T. et al, J. Med. Chem. 1988, 31(4), 779–85.

Kataoka, T. et al, Chem. Pharm. Bull. 1990, 38(4), 874–81.

Warawa et al, Quinuclide Chemistry2[1] Synthesis and Antinflammatory Properites of 2–Substituted Benzhydryl–3–quinclidinols, J. Med. Chem. 17(5), (1974), 497–501.

Sterling et al, Quaternary and Tertiary Quinuclidine Derivatives as Inhibitors of Choline Uptake, J. Pharm. Sciences, 80(8), (1991), 785–789.

Saunders et al, Novel Quinuclidine–Based Ligands for the Muscarinic Cholinergic Receptor, J. Med. Chem 33(4), (1990), 1128–1137.

Turchin et al, Stereochemistry of Quinuclidines containing a Substituent with Aryl(Heteroaryl) Nuclei at Position Three, Khimiko–farmatsevticheskii Zhurnal, 1986, vol. 20, pp. 65–72.

Bondrenko et al, Khim. Farm, 12(11), 1978, pp. 56–60.

Khim. Farm, 7(8), 1973, 20–24.

Ricciardi et al, Facile Synthesis of Styrylquinuclidines, Heterocycles 24, (1986), pp. 971–977.

Khim. Geterosikl, 3, (1983), 381–385.

Mikhlina et al, Synthesis and Properties of (3–Quinuclidyl)Diarycarbinols, Khim. Geterosikl Soedin, 7, 1976, 776–780.

Sekine et al, Effect of Sulfur Containing Purine Nucleosides on Immunological Reaction in Mice, Japan, J. Exp. Med, 1973, vol. 43, 5, pp. 369–375.

DeVito et al, Synthesis and Pharmacological Evaluation of Some Novel 13–[N,N]dialkylamino–alky[benzo][g][2]benzopyrano[43–b]indol–5 [13H]ones, Med, Chem, Res, 1(1) (1991), pp. 47–51.

Emakov et al, Application of Mass Spectrometry in Structural and Stereochemical Investigations., Khim. Geterosikl Soedin, 10 (1975), 1376–1383.

Mikhlina et al, Sterochemistry of Benzo[b]Quinuclidines., Khim. Geterosikl Soedin, 6, (1973), pp. 839–843.

Fleet et al, Complex Quinuclidines (1–Azabicyclo[222] octanes) from Sugars: Synthesis of 1α, 3α, 4α, 5α)–Quinuclidine–3,5,–diol from D–Gluose, J. Chem. Soc, Perkin, Trans, 1(5), (1989), 1067–1068.

QUINUCLIDINE DERIVATIVES AS SQUALENE SYNTHASE INHIBITORS

This application is a 371 of PCT/GB93/02617, Dec. 21, 1993.

This invention concerns heterocyclic-compounds which are useful in inhibiting squalene synthase, processes for their preparation and pharmaceutical compositions containing them. The present invention is also concerned with methods of using such heterocyclic compounds in treating diseases and medical conditions where inhibition of squalene synthase is desirable, for example in treating diseases or medical conditions such as hypercholesterolemia and atherosclerosis.

Several different classes of compounds have been reported to possess the capability of being able to lower cholesterol levels in blood plasma. For example agents which inhibit the enzyme HMG CoA reductase, which is essential for the production of cholesterol, have been reported to reduce levels of serum cholesterol. Illustrative of this class of compounds is the HMG CoA reductase inhibitor known as lovastatin which is disclosed in U.S. Pat. No. 4,231,938. Other agents which are reported to lower serum cholesterol include those which act by complexing with bile acids in the intestinal system and which are hence termed "bile acid sequestrants". It is believed that many of such agents act by sequestering bile acids within the intestinal tract. This results in a lowering of the levels of bile acid circulating in the enteroheptatic system and promoting replacement of bile acids by synthesis in the liver from cholesterol which results in an upregulation of the hepatic LDL receptor and hence in a lowering of circulating blood cholesterol levels.

Squalene synthase (also referred to in the art as squalene synthetase) is a microsomal enzyme which catalyses the first committed step of cholesterol biosynthesis. Two molecules of farnesyl pyrophosphate (FPP) are condensed in the presence of the reduced form of nicotinamide adenine dinucleotide phosphate (NADPH) to form squalene. The inhibition of this committed step to cholesterol should leave unhindered biosynthetic pathways to ubiquinone, dolichol and isopentenyl t-RNA. Elevated cholesterol levels bare known to be one of the main risk factors for ischaemic cardiovacsular disease. Thus, an agent which inhibits squalene synthase should be useful in treating diseases and medical conditions in which a reduction in the levels of cholesterol is desirable, for example hypercholesterolemia and atherosclerosis.

Thus far, the design of squalene synthase inhibitors has concentrated on the preparation of analogues of the substrate farnesyl pyrophosphate (FPP), and hence on compounds which contain phosphorus groups. For example, the preparation of phosphorous-containing squalene synthase inhibitors is reported in published European Patent Application No. 409,181; and the preparation of isoprenoid (phosphinylmethyl)phosphonates as inhibitors of squalene synthase is reported by Biller et al, J. Med. Chem., 1988, 31, 1869. Quinuclidine derivatives are reported in, for example, EP 458,214 to be muscarinic agonists. Recently, certain quinuclidine derivatives have been reported (WO 92/15579 and U.S. Pat. No. 5,135,935) to inhibit squalene synthase.

The present invention is based on the discovery that certain heterocyclic compounds are inhibitors of squalene synthase, and are hence useful in treating diseases and medical conditions in which inhibition of squalene synthase is desirable.

According to the present invention there is provided a compound of formula I (formula set out hereinafter together with the other chemical formulae referred to herein in Roman numerals), or a pharmaceutically acceptable salt thereof, wherein:

$R^1$ is hydrogen or hydroxy;

$R^2$ is hydrogen; or $R^1$ and $R^2$ are joined together so that $CR^1$—$CR^2$ is a double bond;

X is selected from —CH$_2$CH$_2$—, —CH═CH—, —C≡C—, —CH$_2$O—, —OCH$_2$—, —CH$_2$NH—, —NHCH$_2$—, —CH$_2$CO—, —COCH$_2$—, —N═CH—, —CH═N—, —CH$_2$S— and —SCH$_2$— (wherein the sulphur atom in the latter two groups may optionally bear one or two oxygen atoms);

Ar is a heterocyclic moiety containing up to three heteroatoms independently selected from nitrogen, oxygen and sulphur; and wherein Ar may optionally be unsubstituted or may bear one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C)alkylsulphonyl, halogeno-(1–6C)alkyl, (1–6C)alkanoylamino, ureido, N'-(1–6C)alkylureido, (1–6C)alkanoyl and oxime derivatives thereof and O-(1–6C)alkyl ethers of said oxime derivatives;

provided that when $R^1$ is hydroxy, X is not selected from —OCH$_2$—, —N═CH—, —NHCH$_2$— and —SCH$_2$— (optionally bearing one or two oxygen atoms on sulphur); and that when $R^1$ and $R^2$ are both hydrogen, X is —CH$_2$O—, —OCH$_2$—, —CH$_2$S— or —SCH$_2$ (wherein the sulphur atom in the latter two groups optionally bears one or two oxygen atoms) then Ar is not a 5, 6 or 7 membered heteroaryl moiety.

It will be understood that when formula I compounds contain a chiral centre, the compounds of the invention may exist in, and be isolated in, optically active or racemic form. The invention includes any optically active or racemic form of a compound of formula I which possesses the beneficial pharmacological effect of inhibiting squalene synthase. The synthesis of optically active forms may be carried out by standard techniques of organic chemistry well known in the art, for example by, resolution of a racemic form, by synthesis from optically active starting materials or by asymmetric synthesis.

It will also be understood that, insofar as certain of the compounds of the formula I may exhibit the phenomenon of tautomerism, for example a compound of formula I in which Ar bears a hydroxy substituent, the present invention includes any tautomeric form of a compound of formula I which possesses the beneficial pharmacological effect of inhibiting squalene synthase.

It is also to be understood that generic terms such as "alkyl" include both the straight chain and branched chain groups such as butyl and tert-butyl. However, when a specific term such as "butyl" is used, it is specific for the straight chain or "normal" butyl group, branched chain isomers such as "t-butyl" being referred to specifically when intended.

It will also be appreciated that oxime derivatives of the (1–6C)alkanoyl group will comprise aldoximes and ketoximes of formula —C(Ra)═NOH (Ra is H or alkyl), and the O-alkyl ethers of these oximes will have the formula —C(Ra)═NORb (Ra is H or alkyl, and Rb is alkyl).

It will be appreciated that when $R^1$ and $R^2$ are joined so that $CR^1$—$CR^2$ is a double bond, the quinuclidine moiety in formula I will comprise the 2,3-dehydroquinuclidine moiety shown in formula Ia.

Ar, the heterocyclic moiety, encompases monocyclic aromatic heterocycles which contain (in addition to carbon atoms) one, two or three heteroatoms selected from nitrogen, oxygen and sulphur; bicyclic aromatic heterocycles of about 8 to 10 ring atoms and containing (in addition to carbon atoms) one, two or three heteroatoms selected from nitrogen, oxygen and sulphur, and in particular, benz-derivatives of said monocyclic aromatic heterocycles; as well as bicyclic heterocycles which consist of a non-aromatic 5-membered or 6-membered heterocyclic ring containing (in addition to carbon atoms) one, two or three heteroatoms selected from nitrogen, oxygen and sulphur which is fused to a benzene ring. It will be appreciated that the heterocyclic moiety may be attached to $Ar^1$ through any available ring atom.

Suitable values for Ar will therefore include, for example, an aromatic 5-membered or 6-membered heterocyclic ring containing one, two or three heteroatoms selected from nitrogen, oxygen and sulphur, and an aromatic 5-membered or 6-membered heterocyclic ring containing one, two or three heteroatoms selected from nitrogen, oxygen and sulphur which is fused to a benzene ring; or a non-aromatic 5-membered or 6-membered heterocyclic ring containing one, two or three heteroatoms selected from nitrogen, oxygen and sulphur fused to a benzene ring.

A particular value for X is, for example, —CH$_2$CH$_2$—, —CH=CH—, —C≡C—, CH$_2$O, —CH$_2$NH—, —NHCH$_2$—, —CH$_2$CO— or —COCH$_2$—. A more particular value for X is, for example, —CH$_2$CH$_2$—, —CH=CH—, —C≡C— or —CH$_2$O.

A particular value for an optional substituent which may be present on Ar, is, for example, for alkyl; (1–4C)alkyl, such as methyl, ethyl, propyl, isopropyl, butyl, isobutyl or sec-butyl;

for alkenyl; (2–4C)alkenyl, such as allyl, prop-2-enyl, but-2-enyl or 2-methyl-2-propenyl;

for alkynyl; (2–4C)alkynyl, such as prop-2-ynyl or but-2-ynyl;

for alkoxy; (1–4C)alkoxy, such as methoxy, ethoxy, propoxy, isopropoxy or butoxy;

for alkylamino; (1–4C)alkylamino, such as methylamino, ethylamino, propylamino or butylamino;

for di-alkylamino; di-(1–4C)alkylamino, such as dimethylamino, diethylamino, methylpropylamino or dipropylamino;

for alkylcarbamoyl; N-methylcarbamoyl, N-ethylcarbamoyl or N-propylcarbamoyl;

for di-alkylcarbamoyl; di-(1–4C)alkylcarbamoyl, such as N,N-dimethylcarbamoyl or N,N-diethylcarbamoyl;

for alkoxycarbonyl; methoxycarbonyl, ethoxycarbonyl or propoxycarbonyl;

for alkylthio; methylthio, ethylthio, propylthio, isopropylthio or butylthio;

for alkylsulphinyl; methylsulphinyl, ethylsulphinyl, propylsulphinyl, isopropylsulphinyl or butylsulphinyl;

for alkylsulphonyl; methylsulphonyl, ethylsulphonyl, propylsulphonyl, isoproylsulphonyl or butylsulphonyl;

for halogeno; fluoro, chloro, bromo or iodo;

for halogenoalkyl; halogenoalkyl containing one, two or three halo groups selected from fluoro, chloro, bromo and iodo and an alkyl group selected from methyl, ethyl, propyl, iso-propyl, butyl, iso-butyl and sec-butyl, (in particular fluoromethyl, difluoromethyl or trifluoromethyl);

for alkanoyl; formyl, acetyl, propionyl and butyryl;

for alkylureido; N'-methylureido, N'-ethylureido, N'-propylureido,

N'-isoprpoylureido, N'-butylureido, for O-(1–6C)alkyl ethers of alkanoyl oximes; methyl, ethyl, propyl, isopropyl and butyl esters for alkanoylamino; formamido, acetamido, propionamido, iso-propionamido, butyramido or iso-butyramido.

Particular values for Ar include, for example, furyl, pyrrolyl, thienyl, pyridyl, pyrazinyl, primidinyl, pyridazinyl, imidazolyl, oxazolyl, isooxazolyl, thiazolyl, isothiazolyl, oxadiazolyl, 1,2,3-triazolyl, 1,2,4-triazolyl, benzfuranyl, quinolyl, isoquinolyl, benzimidazolyl, indolyl, benzdihydrofuranyl, benzodioxolyl (such as 1,3-benzodioxolyl), and benzdioxanyl (such as 1,4-benzdioxanyl).

In general, it is preferred that Ar is optionally unsubstituted or substituted by one, two or three substituents independently selected from those mentioned above.

In general it is preferred, for example, that $R^1$ is hydroxy and $R^2$ is hydrogen.

In general it is preferred, for example, That X is selected from —CH=CH—, —C≡C— and —CH$_2$O—, especially —C≡C—.

It is generally preferred, for example, that Ar is an aromatic 5-membered or 6-membered heterocyclic ring containing (in addition to carbon atoms) one, two or three heteroatoms selected from nitrogen, oxygen and sulphur which is optionally fused to a benzene ring. More preferably, Ar is a pyridyl or quinolyl moiety (especially pyridyl).

In general it is preferred, for example, that Ar may optionally bear one or more substituents selected from halogeno, hydroxy, nitro, (1–6C)alkyl, (2–6C)alkenyl, (1–6C)alkoxy, (1–6C)alkanoylamino, halogeno-(1–6C) alkyl, (1–6C)alkanoyl and oxime derivatives thereof and O-(1–6C)alkyl ethers of said oximes.

Values of Ar of particular interest include, for example, pyridyl, pyrazinyl, primidinyl, pyridazinyl and imidazolyl (especially pyridyl).

More particular values for Ar include, for example, 2-thienyl, 2-pyridyl, 3-pyridyl, 4-pyridyl, 2-pyrimidyl, 5-pyrimidyl, 3-pyrazinyl, 2-pyridazinyl, 2-imidazolyl, 3-pyrazinyl, 2-pyridazinyl, 1,2,3-triazole-1-yl, 1,2,4-triazol-3-yl, 3-quinolyl, 4-quinolyl, 2-thiazolyl, 5-thiazolyl, 3-isoquinolyl, 4-isoquinolyl, 2-benzimidazolyl, 2-indolyl and 3-indolyl, which may optionally bear one or substituents independently selected from fluoro, chloro, bromo, iodo, hydroxy, nitro, methyl, ethyl, propyl, isopropyl, butyl, isobutyl, sec-butyl, allyl, methoxy, ethoxy, propoxy, isopropoxy, butoxy, formyl, acetyl, propionyl, butyryl and oxime derivaties of the last four groups and O-methyl, ethyl, propyl, isopropyl and butyl ethers of said oximes, acetamido, propionamido, iso-propionamido, fluoromethyl, difluoromethyl and trifluoromethyl.

Values of Ar of particular interest include for example, 2-pyridyl and 3-pyridyl.

Specific values for Ar include, for example, 6-butoxypyrid-3-yl, 3-pyridyl, 5-bromopyrid-2-yl, 3-quinolyl, 2-quinolyl, 5-methylpyrid-2-yl and 5-methoxycarbonylpyrid-2-yl.

In a particular embodiment, when $R^1$ is hydroxy and $R^2$ is hydrogen or $R^1$ and $R^2$ are joined so that $CR^1$—$CR^2$ is a double bond, X is selected from —CH$_2$CH$_2$—, —CH=CH—, —C≡C—, —CH$_2$O—, —CH$_2$NH— and —CH$_2$S (wherein the sulphur atom optionally bears one or two oxygen atoms); and Ar is as herein before defined; and when R$^1$ and R$^2$ are both hydrogen X is selected from —CH$_2$CH$_2$—, —CH=CH— and —C≡C—; and Ar is as hereinbefore defined, provided that Ar is not an imidazolyl moiety.

In particular, R$^1$ is hydroxy and R$^2$ is hydrogen; or R$^1$ and R$^2$ are joined together so that CR$^1$—CR$^2$ is a double bond; X is selected from —CH$_2$CH$_2$—, —CH=CH—, —C≡C—, —CH$_2$O—, —OCH$_2$—, —CH$_2$NH—, —NHCH$_2$—, —CH$_2$CO—, —COCH$_2$—, —N=CH—, —CH=N—, —CH$_2$S— and SCH$_2$— (wherein the sulphur atom in the latter two groups may optionally bear one or two oxygen atoms); or R$^1$ and R$^2$ are both hydrogen and X is selected from —CH$_2$CH$_2$—, —CH=CH—, —C≡C—, —NHCH$_2$—, —CH$_2$NH—, —N=CH—, —CH=N—, —CH$_2$CO— and —COCH$_2$—; Ar is a heterocyclic moiety containing up to three heteroatoms independently selected from nitrogen, oxygen and sulphur; and wherein Ar may optionally be unsubstituted or may bear one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C)alkylsulphonyl, halogeno-(1–6C)alkyl, (1–6C)alkanoylamino, ureido, N'-(1–6C)alkylureido, (1–6C)alkanoyl and oxime derivatives thereof and O-(1–6C)alkyl ethers of said derivatives;

provided that when R$^1$ is hydroxy, X is not selected from —OCH$_2$—, —NHCH$_2$— and —SCH$_2$— (optionally bearing one or two oxygen atoms on sulphur).

In one embodiment of the present invention, R$^1$ and R$^2$ are both hydrogen; and Ar and X have any of the meanings defined above.

In a further embodiment of the present invention, R$^1$ is hydroxy; R$^2$ is hydrogen;

X is selected from —CH$_2$CH$_2$—, —CH=CH—, —C≡C—, —CH$_2$O—, —CH$_2$NH—, —CH=N—, —CH$_2$CO—, —COCH$_2$— and —CH$_2$S— (wherein the sulphur atom in the latter two groups may optionally bear one or two oxygen atoms); Ar is a heterocyclic moiety containing up to three heteroatoms independently selected from nitrogen, oxygen and sulphur; and wherein Ar may optionally be unsubstituted or may bear one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C)alkylsulphonyl, halogeno-(1–6C)alkyl, (1–6C)alkanoylamino, ureido, N'-(1–6C)alkylureido, (1–6C)alkanoyl and oxime derivatives thereof and O-(1–6C)alkyl ethers of said oxime derivatives.

Particular, preferred and specific values are the appropriate values mentioned above.

In a further embodiment of the present invention, R$^1$ and R$^2$ are joined together so that CR$^1$—CR$^2$ is a double bond, and Ar and X are as defined above.

In a particular embodiment the present invention provides a compound of formula I, or a pharmaceutically acceptable salt thereof, wherein:

R$^1$ is hydrogen or hydroxy; R$^2$ is hydrogen; or

R$^1$ and R$^2$ are joined together so that CR$^1$—CR$^2$ is a double bond;

X is selected from —CH$_2$CH$_2$—, —CH=CH—, —C≡C—, —CH$_2$NH— and —NHCH$_2$—.

Ar is a heterocyclic moiety containing one, two or three heteroatoms selected from nitrogen, oxygen and sulphur;

and wherein Ar may optionally be unsubstituted or may bear one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl, (1–6C)alkanoylamino, ureido, N'-(1–6C)alkylureido, (1–6C)alkanoyl and oxime derivatives thereof and O-(1–6C)alkyl ethers of said oxime derivatives; provided that when R$^1$ and R$^2$ are both hydrogen Ar is not an imidazolyl moiety.

Particular, preferred and specific values are the appropriate values mentioned above.

In a further embodiment of interest there is provided a compound of formula I, or a pharmaceutically acceptable salt thereof, wherein:

R$^1$ is hydroxy; R$^2$ is hydrogen; X is selected from —CH$_2$O—, —CH=CH— and —C≡C— (especially —CH=CH— and C≡C—);

Ar is a heteroaryl moiety containing one or two nitrogen atoms (especially pyridyl)

and wherein Ar may optionally be unsubstituted or may bear one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C) alkylamino, di-[(1–6C)alkyl]amino, N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl, (1–6C)alkanoylamino, ureido, N'-(1–6C)alkylureido, (1–6C)alkanoyl and oxime derivatives thereof and O-(1–6C)alkyl ethers of said oxime derivatives.

Particular, preferred and specific values are the appropriate values mentioned above.

In a further embodiment of the present invention there is provided a compound of formula I, or a pharmaceutically-acceptable salt thereof, wherein R$^1$ is hydroxy; R$^2$ is hydrogen; X is —C≡C—; and Ar is a heterocyclic moiety containing one, two or three heteroatoms selected from nitrogen, oxygen and sulphur which is optionally substituted by one, two or three substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, di-N,N-[(1–6C)alkyl]carbamoyl, (1–6C)alkoxycarbonyl, (1–6C)alkylthio, (1–6C) alkylsulphinyl, (1–6C)alkylsulphonyl, halogeno (1–6C) alkyl, (1–6C)alkanoylamino, ureido, N'-(1–6C)alkylureido, (1–6C)alkanoyl and oxime derivatives thereof and O-(1–6C) alkyl ethers of said oxime derivatives.

Particular, preferred and specific values include the appropriate values mentioned above.

Further compounds (and their pharmaceutically-acceptable salts) of particular interest include those in which R$^1$ is hydroxy, R$^2$ is hydrogen, X is —C≡C—, and Ar is a quinoyl or pyridyl moiety (especially a pyridyl moiety) which may optionally be unsubstituted or may bear one, two or three substituents selected from halogeno, hydroxy, nitro, (1–6C)alkyl, (2–6C)alkenyl, (1–6C)alkoxy, (1–6C) alkanoylamino, halogeno (1–6C)alkyl, (1–6C) alkoxycarbonyl, (1–6C)alkanoyl, oxime derivatives thereof and O-(1–6C)alkyl ethers of said oximes.

Compounds of the invention which are of particular interest include the compounds described in the accompanying Examples (and their pharmaceutically-acceptable salts), and are hence provided as a further feature of the present invention.

A suitable pharmaceutically-acceptable salt of the present invention comprises an acid-addition salt derived from an inorganic or organic acid which provides a pharmaceutically-acceptable anion. Thus, examples of salts of the present invention include acid-addition salts with hydrochloric, hydrobromic, nitric, sulphuric, phosphoric, trifluoroacetic, citric, tartaric, succinic, maleic, fumaric or acetic acid. In addition, suitable pharmaceutically-acceptable salts include [where the compound of formula I is sufficiently acidic, for example where the compound of formula I bears an acidic substituent such as carboxy] those formed with a base which affords a pharmaceutically acceptable cation. Suitable bases include an alkali metal salt (such as a sodium or potassium salt), an alkaline earth metal salt (such as a calcium or magnesium salt), an ammonium salt or a salt with an organic base which affords a physiologically-acceptable cation such as a salt with methylamine, dimethylamine, triethylamine, piperidine or morpholine.

The compounds of the present invention may be obtained by standard procedures of organic chemistry already known to be applicable to the preparation of structurally analogous compounds. Such procedures for the preparation of the compounds of formula I, or pharmaceutically acceptable salts thereof, are provided as a further feature of the present invention and are illustrated by the following preferred processes in which the various generic radicals, for example, $R^1$, $R^2$, X Ar may take any of the meanings hereinbefore defined.

Thus, according to the present invention there is also provided a process for preparing a compound of formula I, or a pharmaceutically-acceptable salt thereof, which process comprises:

(a) For those compounds of formula I in which $R^1$ and $R^2$ are both hydrogen, reducing a compound of formula I in which $R^1$ and $R^2$ are joined together so that $CR^1$—$CR^2$ is a double bond (provided that X is not —CH=CH— or —C≡C—).

The reduction may be carried out, for example, by catalytic hydrogenation, or by reaction with a suitable reducing agent. Suitable reaction conditions include, for example, catalytic hydrogenation using a catalyst which comprises a noble metal. Particular catalysts include palladium, platinum and nickel (especially when in the finely divided state known as raney nickel), and catalysts in which the noble metal is supported on an inert carrier such as carbon. A specific example of a supported catalyst is Pd/C. The reduction is conveniently carried out in a solvent of, for example, an alcohol (such as ethanol), and at (or near) ambient temperature and optionally under pressure.

Further suitable reaction conditions include, for example, reduction with a borane such as diborane. The reaction is generally carried out in an inert solvent of, for example, tetrahydrofuran or methyl t-butyl ether at, for example, 0°–60° C. It may be preferable to cool the reaction below ambient temperature (eg. to about 0° C.) during the reduction. The borane generated may be hydrolysed by treatment with an organic acid such as acetic acid, which hydrolysis may be carried out at 0°–60° C., and may be accelerated by heating (eg. refluxing).

(b) For compounds of formula I in which $R^1$ and $R^2$ are joined together so that $CR^1$—$CR^2$ is a double bond, dehydrating a compound of formula I in which $R^1$ is hydroxy and $R^2$ is hydrogen.

The dehydration may be carried out using an acid such as sulphuric acid (eg. concentrated sulphuric acid), or p-toluene sulphonic acid. The reaction is conveniently carried out with heating, and conveniently an inert solvent is employed. For example, the reaction may be carried out using sulphuric acid at temperatures of about 70°–130° C.; or using p-toluene sulphonic acid in a hydrocarbon solvent of, for example, toluene or xylene at ambient temperature to reflux, and preferably at reflux. The dehydration may also be carried out using trifluoroacetic acid in an inert solvent such as dichloromethane (at ambient temperature to reflux temperature).

(c) For compounds of formula I in which $R^1$ and $R^2$ are joined together so that $CR^1$—$CR^2$ is a double bond, treating a compound of formula II in which Z is a leaving group with a base.

Suitable values for Z include, for example, halogen such as chloro, bromo, iodo, or a methylsulphonyloxy or toluenesulphonyloxy group. Suitable bases include hydroxide (such as potassium or sodium hydroxide), and alkoxide (such as potassium t-butoxide or sodium ethoxide).

The reaction is conveniently carried out in the presence of a solvent, preferably a polar organic solvent. Suitable solvents include, for example, an alcohol (such as ethanol), or an aprotic solvent such as dimethylformamide or N-methylpyrrolidone. The reaction may be carried out at ambient temperature or at an elevated temperature, such as at a temperature between ambient and the reflux temperature of the reaction mixture. This method is generally preferred over that described in (b) when X is —OCH$_2$— or —SCH$_2$—.

The compounds of formula II may be prepared from a compound of formula I in which $R^1$ is hydroxy. For example, where Z is halogen the compound of formula I in which $R^1$ is hydroxy and $R^2$ is hydrogen may be reacted with the appropriate phosphorous halide (eg. PCl$_5$, PBr$_3$ or PI$_3$), or where Z is chloro, by reaction with thionyl chloride. The compound of formula I in which $R^1$ is hydroxy may be reacted with mesyl chloride to the compound in which Z is methylsulphonyloxy; and with tosyl chloride to give Z is toluene sulphonyloxy.

(d) For those compounds of formula I in which X is —CH$_2$CO—, reacting an organometallic compound of formula Ar—M in which M is a metal atom or a derivative thereof, with a compound of formula III.

Suitable values for M include, for example, magnesium and lithium. In the case where M is magnesium it is conveniently present in the form of a derivative of formula —MgX where X is a halogen atom such as iodo or bromo, so that the organometallic compound has the formula Ar—MgX and is in the form known as a Grignard Reagent. The reaction is generally carried out in an inert solvent such as dry diethyl ether or tetrahydrofuran. For example, the reaction may be carried out at a temperature between 0° C. and the reflux temperature of the reaction mixture.

The compounds of formula Ar—M may be prepared from the corresponding compound of formula Ar—"hal" in which "hal" is a halogen atom, such as iodo or bromo as is well known in the art.

e) For those compounds of formula I in which X is —$CH_2$—NH— or —$NHCH_2$—, reducing a compound of formula I in which X is —CH=N— or —N=CH— (as appropriate).

The reaction may be carried out using a chemical reducing agent such as a hydride in a solvent such as an alcohol at ambient temperature. Thus, in a particular example, the reduction may be carried out using sodium borohydride in a solvent of methanol at ambient temperature. The reduction may also be carried out by selective catalytic hydrogenation using similar conditions to those described under (a) above.

It will be appreciated that the preferred method of reduction will depend upon the value of X. Thus, for example, where debenzylation is possible (eg. when X is —$NHCH_2$—), it is generally preferred that a chemical reducing agent is employed.

The compounds of formula I in which X is —CH=N— may be prepared by reaction of a compound of formula IV with a compound of formula Ar—$NH_2$. The reaction is generally carried out in an inert hydrocarbon solvent such as toluene or benzene, with heating (eg. at reflux) and the reaction may be accelerated by removing water generated in the reaction by azeotropic distillation. Similarly, the compounds of formula I in which X is —N=CH— may be prepared by reaction of a compound of formula Ar—CHO with a compound of formula V.

f) For those compounds of formula I in which X is —$CH_2NH$—, —$CH_2O$—, —$CH_2S$—, $R^1$ is hydroxy and $R^2$ is hydrogen, reacting a compound of formula Ar—Z in which Z is —$NH_2$, —OH or SH as appropriate with a compound of formula VI.

The reaction is conveniently carried out in a solvent such an inert hydrocarbon eg. toluene with heating. The reaction may be facilitated by the presence of acid or base.

The compound of formula VI is conveniently generated in situ, by, for example, treating quinuclidin-3-one with trimethylsulphoxonium iodide in the presence of a base of, for example, an alkali metal hydride such as sodium hydride and in a solvent such as dimethylformamide, or an alkali metal hydroxide such as sodium hydroxide in a solvent such as an aqueous solvent.

The compound of formula VI may also be prepared from a "halohydrin" as is well known in the art. The halohydrin may be prepared, for example, by addition of HOCl to the corresponding olefin and the halohydrin treated with base (eg. NaOH) to give the compound of formula VI.

g) For compounds of formula I in which X is —CH=CH—, reacting a compound of formula Ar—CH2—$P^+Ph_3W^-$ with a compound of formula IV in the presence of a base.

Suitable bases include alkoxides, such as potassium t-butoxide, and the reaction is conveniently carried out in an inert solvent such as tetrahydrofuran with cooling below ambient temperature eg –40° C. to 0° C.); and metal hydrides such as sodium hydride in a solvent such as dimthyl formamide or dimethylsuphoxide. A particularly suitable base is, for example, sodium dimsyl which may conveniently be used in a solvent such as dimethyl suphoxide.

The compounds of formula Ar—CH2—$P^+Ph_3W^-$ may be prepared by reaction of a compound of formula $ArCH_2$—hal in which "hal" is halogen, such as chloro, with triphenylphosphine as is well known in the art.

h) For those compounds of formula I in which X is —$CH_2CH_2$—, reducing a compound of formula I in which X is —CH=CH— or in which X is —C≡C—.

The reaction may conveniently be carried out by catalytic hydrogenation using conditions similar to those mentioned in (a) above.

In an alternative synthesis a compound of formula $ArCH_2CH_2$—hal wherein "hal" represents a halogen atom such as bromo, is reacted with quinuclidin-3-one in the presence of sec-butyl lithium, with cooling (eg –70° C.) in an inert solvent such as tetrahydrofuran.

i) For compounds of formula I in which X is —$COCH_2$—, reacting a compound of formula Ar—$CH_2M$ in which M is a metal atom or a derivative thereof, with a compound of formula VII.

Suitable values for M and suitable reaction conditions are those mentioned in (d) above. The compounds of formula Ar—$CH_2M$ may be prepared from the corresponding halogeno compound in a manner analogous to the preparation of compounds of formula Ar—M discussed in (d) above.

j) For those compounds of formula I in which X is —$CH_2O$— or —$CH_2S$—, reacting a compound of formula $ArCH2Z^1$ with a compound of formula VIII, in which $Z^1$ is a leaving group and $Z^2$ is —YM, or $Z^1$ is —YM and $Z^2$ is a leaving group, and wherein Y is oxygen or sulphur (as appropriate) and M is a metal atom.

Suitable leaving groups include, for example, halogen (such as chloro, bromo or iodo), methanesulphonyloxy, toluenesulphonyloxy or trifluoromethanesulphonyloxy;.and suitable metals include, for example sodium and lithium.

The process is generally performed in the presence of a suitable solvent, for example, a hydrocarbon, such as toluene or xylene, or an ether such as dioxan or tetrahydrofuran, and at a temperature in the range, for example 20°–150° C.

It may be desirable to protect the quinuclidine nitrogen atom during the reaction, especially when $Z^1$ is —YM, as described in (1) below. It may be desirable to protect $R^1$ when it represents a hydroxy group as, for example, a silyl ether.

k) For those compounds of formula I in which X is —$OCH_2$— or —$SCH_2$— and $R^1$ and $R^2$ are both hydrogen, reacting a compound of formula ArYH in which Y is oxygen or sulphur as appropriate with a compound of formula IX in which Z is a leaving group.

Suitable leaving groups include halogen, such as chloro, bromo or iodo, methanesulphonyloxy and toluenesulphonyloxy. The reaction is generally carried out in the presence of a base such as an alkali metal hydroxide, eg sodium or potassium hydroxide, and in a solvent such as dimethylsulphoxide or dimethylformamide.

l) For compounds of formula I in which X is —$OCH_2$—, —$SCH_2$—, —CH2O—, or —$CH_2S$—, deprotecting a compound of formula X in which Q is a protecting group.

Suitable values for Q include, for example, —$BH_3$ or an oxygen atom. When Q is —$BH_3$ the deprotection may be carried out by treatment with an acid such as hydrochloric acid in a solvent such as acetone. Q is an oxygen atom deprotection may be carried out by reduction using a suitable reducing agent such as sulphur dioxide.

The compounds of formula X in which X is —$CH_2O$— or —$CH_2S$— may be prepared by methods analogous to those described in (j), and in which X is —$OCH_2$— or —$SCH_2$— by methods analogous to those described in (k) above, but in which the starting material containing the quinuclidine moiety is protected by Q. A preferred way of preparing compounds of formula X in which X is —$CH_2O$— or —$CH_2S$— and $R^1$ is hydroxy and $R^2$ is hydrogen is by a procedure analogous to that described in (f) in which the compound of formula X is protected by Q. The quinuclidine moiety in the various starting materials may be protected using methodology well known in the art. Thus, for example, those in which Q is $BH_3$ may be prepared by reaction of the appropriate quinuclidine moiety with BH$_3$.THF, generally with cooling (for example at −70° C.); whilst those in which Q is an oxygen atom may be prepared by oxidation of the appropriate quinuclidine moiety with, for example, 30% hydrogen peroxide.

m) For those compounds of formula I in which X is —C≡C—, reacting a compound of formula I in which X is —CH=CH— with a halogen, followed by treatment with a base.

A suitable halogen is bromine and the reaction is conveniently carried out in an inert solvent such as carbon tetrachloride. Suitable bases include, for example, potassium t-butoxide. This treatment is conveniently carried out in a solvent such as THF, with heating (eg. at a temperature between ambient and about 70° C.).

n) For those compounds of formula I in which $R^1$ is hydroxy, $R^2$ is hydrogen and X is —C≡C—, reacting a compound of formula Ar—C≡C—M in which M is a metal atom, with quinuclidin-3-one.

A suitable metal is lithium and suitable reaction conditions include those mentioned in (d) above.

o) For those compounds in which $R^1$ and $R^2$ are hydrogen and X is —C≡C—, reacting a compound of formula Ar—C≡C—M in which M is a metal atom with a compound of formula VIII in which Z is a leaving group.

Suitable values for Z include, for example, halogen (such as chloro, bromo or iodo), methanesulphonyloxy, toluenesulphonyloxy or trifluoromethanesulphonyloxy; suitable values for M include, for example, lithium; and suitable reaction conditions include those mentioned under (d) above.

p) For those compounds in which X is —C≡C—, and $R^1$ is hydrogen or hydroxy and $R^2$ is hydrogen, reacting a compound of formula XI with a compound of formula Ar—Z in which Z is a leaving group in the presence of a catalyst.

Suitable catalysts include, for example, transition metal complexes such as palladium or nickel complexes. Particular catalysts are palladium (II) complexes, a specific example of which is Pd(PPh$_3$)$_2$Cl$_2$. Suitable values for Z include, for example, halogen (such as chloro, bromo or iodo), methanesulphonyloxy, toluenesulphonyloxy and trifluoromethanesulphonyloxy. The reaction is generally carried out in the presence of a base, for example, an amine such as triethylamine and in a solvent such as dimethylformamide with heating (for example at 60° to 100° C.). The reaction is preferably carried out in the prersence of copper (I)iodide. Compounds of formula XX may be prepared according to Scheme 1a and 2b.

q) For those compounds in which X is —C=C— and $R^1$ is hydrogen or hydroxy and $R^2$ is hydrogen, reacting a compound of formula XII with a compound of formula Ar—Z in which Z is a leaving group in the presence of a catalyst.

Suitable reaction conditions are those mentioned under (p) above. Compounds of formula XII may be prepared according to Scheme 1b and 2a.

r) For those compounds of formula I in which X is —CH$_2$CH$_2$— or —CH=CH—, reducing a compound of formula I in which X is —C=C—.

The reaction may conveniently be carried out by catalytic hydrogenation using conditions similar to those mentioned in (a) above.

When a compound of formula I is desired in which X is —CH=CH—, a selective catalyst is preferably employed such as palladium which has been deposited on barium sulphate and then treated with quinoline ("Lindlars catalyst").

s) For those compounds of formula I in which X is —SCH$_2$— or —CH$_2$S— wherein the sulphur atom bears one or two oxygen atoms, oxidising the corresponding compound of formula I in which X is —SCH$_2$— or —CH$_2$S—.

The compounds of formula I in which X is —SCH$_2$— may be be oxidised to these in which the sulphur atom bears an oxygen atom (that is to a "sulphoxide") using, for example an appropriate quantity of sodium periodate. Further oxidation to the compound in which the sulphur atom bears two oxygen atoms (that is a "sulphone") may be carried out using a peracid such as peracetic acid or hydrogen peroxide. The oxidation of sulphur compounds to the corresponding sulphoxides and sulphones is well known in the chemical art. Compounds of formula I in which X is —CH$_2$S— may be oxidised to the corresponding sulphoxides or sulphones in the same way.

In some cases oxidation of compounds of formula I to give a sulphone may be accompanied by some oxidation of the nitrogen atom in the quinuclidine ring to the N-oxide. In such cases the quinuclidine N-oxide moiety may be reduced back to a quinuclidine moiety without affecting the sulphone using reducing agents well known in the art, such as sulphur dioxide.

It will be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein. Suitable protecting groups for hydroxy include, for example, silyl groups such as trimethylsilyl or t-butyldimethylsilyl, tetrahydropyranyl and esterifying groups such as a methyl or ethyl ester; and for amino groups include benzyloxycarbonyl and t-butoxycarbonyl. Carboxy groups may be protected in a reduced form such as in the form of the corresponding protected alcohol, which may be subsequently oxidised to give the carboxy group. The protecting groups may be removed at any convenient stage in the synthesis using conventional techniques well known in the chemical art.

It will also be appreciated that the preferred process for preparing a particular compound of formula I will depend upon the nature of the various radicals. Similarly, the preferred choice of reagent will depend upon the nature of the various radicals present. For example, when it is required to reduce a particular compound the reducing agent will generally be selected to be one which does not interfere with other groupings present.

It will also be appreciated that certain of the various optional substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of, substituents. The reagents and reaction conditions for such procedures are well known in the chemical art. Particular examples of aromatic substitution reactions include the introduction of a nitro group using concentrated nitric acid, the introduction of an acyl group using, for example, an acylhalide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

When a pharmaceutically-acceptable salt of a compound of the formula I is required, it may be obtained, for example, by reaction of said compound with the appropriate acid (which affords a physiologically acceptable anion), or with the appropriate base (which affords a physiologically acceptable cation), or by any other conventional salt formation procedure.

As mentioned previously, the compounds of the formula I (and their pharmaceutically-acceptable salts) are inhibitors of the enzyme squalene synthase. Thus the compounds of the present invention are capable of inhibiting cholesterol biosynthesis by inhibition of de novo squalene production.

The beneficial pharmacological properties of the compounds of the present invention may be demonstrated using one or more of the following techniques.

(a) Inhibition of Squalene synthase

In this test, the ability of a compound to prevent the formation of squalene from a radioactive substrate (tritiated farnesyl pyrophosphate) is assessed.

The test compound is incubated at a concentration of 25 micromolar in 200 µl of a buffered solution containing potassium phosphate (50 mM), $MgCl_2$ (4.95 mM), KF (9.9 mM), NADPH (0.9 mM) and rat liver microsomal protein (20 µg). Rat liver microsomes are prepared by the method described in published European Patent Application No. 324,421 and stored in liquid nitrogen prior to assay. Assay vials are kept at 37° C. throughout the incubation.

The reaction is started with the addition of the substrate (1-[$^3$H]-farnesyl pyrophosphate), final concentration 20 µM, and stopped after 15 minutes reaction time with the addition of 50 µl of 4% KOH. The reaction products are separated from unreacted substrate after application to a C-18 octadecyl 1 ccBond column (Analytichem Int product No. 617101). An aqueous fraction is eluted with 250 µl of 0.1M KOH. Squalene is then eluted with 1.0 ml 10% ethylacetate in hexane and radioactivity determined. The difference in radioactivity in the presence and absence of the test compound is used to determine the level of inhibition. If the test compound inhibits at greater than about 70% at 25 micromolar, it is generally re-tested at 25 and 2.5 micromolar. The $IC_{50}$ (concentration which results in a 50% inhibition of squalene production), of the test compound can be determined by testing the compound at several, for example five, concentrations predicted from the two concentration results. The $IC_{50}$ can then be determined from a plot of percentage inhibition against concentration of test compound.

In general, compounds of formula I show significant inhibition in the above test at a concentration in the range of about 0.001 to 25 µM.

By way of illustration of the squalene synthase inhibitory properties of the compounds of formula I, the compound of formula I described in Example 1 below gave about 99% inhibition at 2.5 µM.

(b) Acute rat cholesterol synthesis assay.

This is an acute in vivo test in the rat to measure de novo hepatic cholesterol synthesis from exogenously administered $^{14}$C-acetate.

Female rats (35–55 g) are housed in reverse lighting conditions (red light from 0200 h–1400 h) for a period of about 2 weeks prior to test. Animals are allowed free access to chow and drinking water throughout this period. At test, animals should weigh 125–150 g.

Test compounds may be administered by oral gavage, dissolved or suspended in 0.5% polysorbate, or by ip or iv dosing. Control animals receive vehicle alone. After 1 hour the rats are injected ip with 25 µCi [2-$^{14}$C]-acetate (NEN DUPONT. specific activity, 45–60 mCi/mmol NEC-085H, or AMERSHAM specific activity, 50–60 mCi/mmol CFA 14) in a volume of 0.25 ml saline (100 µCi/ml). After a further hour, rats are terminally anaesthetised with halothane and a blood sample obtained from the abdominal vena cava.

1 ml of plasma is lyophilised and then saponified in 2 ml ethanolic KOH (1 part 33% KOH, 9 parts ethanol) at 75° C. for 2 hours. After addition of an equal quantity of water, non-saponifiable lipids are extracted with two 5 ml volumes of hexane. The hexane extracts are evaporated to dryness and the residues dissolved in ethanol to determine cholesterol specific radioactivity. $ED_{50}$ values can be determined in the standard way.

In general, compounds of formula I show activity in the range of about 0.1 to 100 mg/kg.

By way of illustration, the compound of formula I described in Example 1 gave a 71% decrease in the rate of cholesterol biosynthesis.

In an alternative in vivo test, de novo hepatic cholesterol synthesis from exogenously administered $^3$H-mevalonolactone is measured. The above procedure is used but with $^3$H-mevalonolactone (2.5 µCi) administered in place of $^{14}$C-acetate and the test compound is generally administered as a solution or suspension in 10% dimethylsulphoxide in 0.5% hydroxypropylmethylcellulose.

No overt toxicity was detected when compounds of the formula I were administered at several multiples of their minimum inhibitory dose or concentration.

When used in the treatment of diseases and medical conditions in which an inhibition of cholesterol biosynthesis is desired, for example in the treatment of hypercholesterolemia or atherosclerosis, it is envisaged that a compound of formula I (or a pharmaceutically acceptable salt thereof) will be administered orally, intravenously, or by some other medically acceptable route so that a dose in the general range of, for example, 0.01 to 50 mg per kg body weight is received. However it will be understood that the precise dose administered will necessarily vary according to the nature and severity of the disease, the age and sex of the patient being treated and the route of administration.

In general, the compounds of formula I (or a pharmaceutically-acceptable salt thereof) will usually be administered in the form of a pharmaceutical composition, that is together with a pharmaceutically acceptable diluent or carrier, and such a composition is provided as a further feature of the present invention.

A pharmaceutical composition of the present invention may be in a variety of dosage forms. For example, it may be in the form of tablets, capsules, solutions or suspensions for oral administration, in the form of a suppository for rectal administration; in the form of a sterile solution or suspension for parenteral administration such as by intravenous or intramuscular injection.

A composition may be obtained by conventional procedures using pharmaceutically acceptable diluents and carriers well known in the art. Tablets and capsules for oral administration may conveniently be formed with a coating, such as an enteric coating (for example, one based on cellulose acetate phthalate), to minimise dissolution of the active ingredient of formula I (or a pharmaceutically-acceptable salt thereof) in the stomach or to mask unpleasant taste.

As mentioned above, the compounds of the present invention are squalene synthase inhibitors and hence possess the property of inhibiting cholesterol biosynthesis. Thus the compounds of the present invention will be useful in treating diseases or medical conditions in which an inhibition of squalene synthase is desirable, for example those in which a lowering of the level of cholesterol is blood plasma is desirable. In particular, the compounds of the present invention will be useful in treating hypercholesterolemia and/or ischaemic diseases associated with atheromatous vascular degeneration such as atherosclerosis. The compounds of the present invention will also be useful in treating fungal infections.

According to a further feature of the present invention there is provided a method of inhibiting squalene synthase in a warm-blooded animals (such as man) requiring such treatment, which method comprises administering to said animal an effective amount of a compound of formula I or a pharmaceutically-acceptable salt thereof wherein:

$R^1$ is hydrogen or hydroxy;

$R^2$ is hydrogen; or $R^1$ and $R^2$ are joined together so that $CR^1$—$CR^2$ is a double bond;

X is selected from —$CH_2CH_2$—, —CH=CH—, —C≡C—, —$CH_2O$—, —$OCH_2$—, —$CH_2NH$—, —CH=N—, —N=CH—, —$NHCH_2$—, —$CH_2CO$—, —$COCH_2$—, —$CH_2S$— and —$SCH_2$— (wherein the sulphur atom in the latter two groups may optionally bear one or two oxygen atoms);

Ar is a heterocyclic moiety containing up to three heteroatoms independently selected from nitrogen, oxygen and sulphur;

and wherein of Ar may optionally be unsubstituted or may bear one or more substituents independently selected from halogeno, hydroxy, amino, nitro, cyano, carboxy, carbamoyl, (1–6C)alkyl, (2–6C)alkenyl, (2–6C) alkynyl, (1–6C) alkoxy, (1–6C) alkylamino, di-[(1–6C) alkyl]amino, N-(1–6C) alkylcarbamoyl, di-N, N-[(1–6C)alkyl]carbamoyl, (1–6C) alkoxycarbonyl, (1–6C) alkylthio, (1–6C) alkylsulphinyl, (1–6C) alkylsulphonyl, halogeno-(1–6C)alkyl, (1–6C) alkanoylamino, (1–6C)alkanoyl and oxime derivatives thereof and O-(1–6C)alkyl ethers of said oxime derivatives;

provided that when $R^1$ is hydroxy, X is not selected from —$OCH_2$—, —$NHCH_2$—, —N=CH—, and —$SCH_2$—.

Particular, preferred and specific values include those mentioned above.

In particular, the present invention provides a method of inhibiting cholesterol biosynthesis, and more particularly to a method of treating hypercholesterolemia and atheromatous vascular degeneration (such as atherosclerosis).

Thus the present invention also provides the use of a compound of formula I (as herein defined), or a pharmaceutically-acceptable salt thereof, for the manufacture of a medicament for treating diseases or medical conditions in which a lowering of the level of cholesterol in blood plasma is desirable (such as hypercholesterolemia and atherosclerosis).

The compounds of the present invention may, if desired, be administered together with (or sequentially to) one or more other pharmacological agents known to be useful in the treatment of cardiovascular disease, for example, together with agents such as HMG-CoA reductase inhibitors, bile acid sequestrants, other hypocholesterolaemic agents such as fibrates, for example gemfibrozil, and drugs for the treatment of coronary heart disease. As a further example, the compounds of the present invention may, if desired, be administered together with (or sequentially to) an angiotensin converting enzyme (ACE) inhibitor, such as captopril, lisinopril, zofenopril or enalapril.

Compounds which inhibit squalene synthase have also found utility as antifungal agents. Thus the present invnetion also provides a method of treating fungal infections comprising adimistering a compound of formula I, or a non-toxic salt thereof, to an organism in need of such treatment.

In particular, the present invention-also provides a method of treating fungal infections which comprises administration to an a warm blooded animal, such as man, in need of such treatment an effective amount of a compound of formula I, or a pharmaceutically acceptable salt thereof.

When used as anti-fungal agents the compounds may be formulated in a variety of ways, the nature of such formulation depending on whether the use is for controlling pathogens infecting mammals such as man, or in agriculture such as in soil or plants, or some other object. For medical applications, the compounds of the present invention may, in addition to the formulations mentioned above, be adapted for topical administration and such a composition is provided as a further feature of the present invention. Such compositions may be in a variety of forms, for example creams or lotions.

The invention will now be illustrated by the following non-limiting Examples in which, unless otherwise stated:

(i) evaporations were carried out by rotary evaporation in vacuo;

(ii) operations were carried out at room temperature, that is in the range 18°–26° C.;

(iii) flash column chromatography or medium pressure liquid chromatography (MPLC) was performed on silica gel (Merck Kieselgel Art.9385, obtained from E Merck, Darmstadt, Germany);

(iv) yields are given for illustration only and are not necessariliy the maximum attainable by diligent process development;

(v) proton NMR spectra were normally determined at 200 MHz using tetramethylsilane (TMS) as an internal standard, and are expressed as chemical shifts (delta values) in parts per million relative to TMS using conventional abbreviations for designation of major peaks: s, singlet, m, multiplet; t, triplet; br, broad; d, doublet;

(vi) all end-products were characterised by microanalysis, NMR and/or mass spectroscopy; and (vii) conventional abbreviations are used for individual radicals and recrystallisation solvents, for example, Me=methyl, Et=ethyl, Pr=Propyl, $Pr^i$=isopropyl, Bu=butyl, $Bu^i$=isobutyl, Ph=phenyl; EtOAc=ethyl acetate, $Et_2O$=ether, MeCN=acetonitrile, MeOH= methanol, EtOH=ethanol, $Pr^iOH$=2-propanol, $H_2O$= water.

EXAMPLE 1

A stirred mixture of 3-ethynyl-3-hydroxyquinuclidine (600 mg), 5-bromo-2-n-butoxypyridine (920 mg), bis-(triphenylphosphine)-palladium (II) chloride (140 mg), copper (I) iodide (70 mg) and dry triethylamine (10 ml) in dry dimethylformamide (20 ml) was heated at 90° C. under an atmosphere of argon for 6 hours. The reaction mixture was cooled and the dimethylformamide and triethylamine were removed by evaporation. The residue was treated with 2M aqueous sodium hydroxide solution (20 ml) and the resulting mixture extracted with dichloromethane (3×20 ml). The organic extracts were combined, dried (MgSO$_4$) and evaporated to give a brown residue which was crystallised from acetonitrile to yield 3-[2-(6-butoxy-3-pyridyl)ethynyl]quinuclidin-3-ol (300 mg) as a solid, m.p. 149°–151° C.; microanalysis, found: C, 71.3; H, 7.9; N, 8.9%; C$_{18}$H$_{24}$N$_2$O$_2$.1H$_2$O requires: C, 71.47; H, 8.08; N, 9.26%; NMR (DHSOd$_6$): 0.9–1.0(3H, t), 1.2–1.35(1H, m), 1.35–1.5 (2H, m), 1.5–1.65(1H, m), 1.65–1.75(2H, m), 1.75–2.0(3H, m), 2.6–2.75(4H, t), 2.8–2.85(1H, d), 3.02–3.17(1H, d), 4.2–4.3(2H, t), 5.55(1H, s), 6.75–6.83(1H, d), 7.65–7.72 (1H, d) and 8.2(1H, s); m/Z 301 (M+H).

The 5-bromo-2-n-butoxypyridine used as a starting material was prepared as follows:

Sodium hydride (60% w/v dispersion in mineral oil; 1.8 g) was added in portions over 20 minutes to n-butanol (100 ml) with stirring. The mixture was then stirred until no further hydrogen evolution was noted. 2,5-Dibromopyridine (7.1 g) was added and the resulting mixture stirred at reflux for 6 hours. After cooling, the n-butanal was removed by evaporation and the residue was treated with water (50 ml) and extracted with dichloromethane (2×20 ml). The organic extracts were combined, washed with water (20 ml), dried (MgSO4) and evaporated to give 5-bromo-2-n-butoxypyridine (6.3) as a pale yellow oil, NMR (DHSOd$_6$): 0.9–0.96(3H, t), 1.32–1.5(2H, m), 1.62–1.76(2H, m), 4.2–4.28(2H, t), 6.79–6.82(1H, d), 7.85–7.9(1H, d of d) and 8.26(1H, d).

The 3-ethynyl-3-hydroxyquinuclidine used as starting material was obtained as follows:

A solution of n-butyl lithium (100 ml of a 2M solution in pentane) was added portion-wise over a period of 20 minutes to a stirred solution of ethynyltrimethylsilane (19.6 g) in dry tetrahydrofuran (400 ml) at −70° C. The mixture was stirred for 1 hour at −70° C. A solution of quinuclidin-3-one (2.4 g) in dry tetrahydrofuran (100 ml) was then added to the mixture and the mixture stirred for 1 hour at −70° C. Methanol (1 ml) was then added to the mixture and the mixture allowed to warm to room temperature. The solvents were removed by evaporation. Methanol (500 ml) and potassium carbonate (40 g) were added to the residue and the mixture was stirred for 1 hour. The solvent was removed by evaporation. The residue was triturated under water (500 ml) and the solid obtained dried in vacuo. There was thus obtained 3-ethynyl-3-hydroxy-quinuclidine as a solid, m.p. 193°–197° C.; NMR (DMSO-d$_6$): 1.5–1.3(1H, m), 1.4–1.6 (1H, m), 1.7–1.95(3H, m), 2.55–2.8(5H, m), 2.95(1H, d), 3.3(1H, d) and 5.4(1H, s); m/Z 152 (M+H).

EXAMPLE 2

The procedure described in Example 1 was repeated using 3-bromopyridine in place of 5-bromo-2-n-butoxypyridine. Purification by flash chromatography on silica gel using 10% methanol in dichloromethane containing 1% ammonia (density, 0.88 g/cm$^3$) as eluent, followed by recrystallisation from a mixture of propan-2-ol and diethyl ether, gave 3-[2-(3-pyridyl)ethynyl]quinuclidin-3-ol which was treated with ethereal hydrogen chloride to give 3-[2-(3-pyridyl)ethynyl]quinuclidin-3-ol hydrochloride, NMR(DMSOd$_6$): 1.7–1.85(1H,m), 1.87–2.05(1H,m), 2.05–2.26(2H,m), 2.3 (1H,br), 3.05–3.39(3H,m), 3.65(1H,d), 5.1(1H,br+HO), 7.65(2H,m), 8.12(1H,br), 8.65(1H,br), 8.85(1H,br) and 10.6 (1H,br).

EXAMPLE 3

The procedure described in Example 1 was repeated using 2,5-dibromopyridine in place of 5-bromo-2-n-butoxypyridine. Purification by flash chromatography on silica gel using 10% methanol in dichloromethane containing 1% ammonia (density, 0.88 g/cm$^3$) as eluent, gave 3-[2-(5-bromopyrid-2-yl)ethynyl]quinuclidin-3-ol as a solid, m.p. 194°–198° C.; NMR(DHSOd$_6$): 1.25–1.42(1H, m), 1.55–1.72(1H,m), 1.80–2.0(2H,m), 2.02(1H,br), 2.75 (4H,t), 2.9(1H,d), 3.16(1H,d), 5.18(1H,s), 7.45(1H,d), 8.05 (1H,d of d) and 8.67(1H,d).

EXAMPLE 4

The procedure described in Example 1 was repeated using 3-bromoquinoline in place of 5-bromo-2-n-butoxypyridine to give, after crystallisation from a mixture of dichloromethane and n-hexane, 3-[2-(3-quinolyl)ethynyl]quinuclidin-3-ol as a solid, m.p. 194°–198° C.; NMR (DMSOd$_6$, 100° C.): 1.25–1.42(1H,m), 1.55–1.72(1H,m), 1.8–2.0(2H,m), 2.02(1H,br), 2.75(4H,t), 2.9(1H,d), 3.16 (1H,d), 5.65(1H,s), 7.43–7.55(1H,m), 7.6–7.7(1H,m), 7.82–7.92(2H,m), 8.35(1H,d) and 8.72(1H,s).

EXAMPLE 5

The procedure described in Example 1 was repeated using 2-iodoquinoline in place of 5-bromo-2-n-butoxypyridine. Purification by flash chromatography on silica gel using 10% methanol in dichloromethane containing 1% ammonia (density, 0.88 g/cm$^3$) as eluent gave 3-[2-(2-quinolyl)ethynyl]quinuclidin-3-ol; NMR(DHSOd$_6$): 1.25–1.42(1H, m), 1.55–1.72(1H,m), 1.8–2.0(2H,m), 2.02(1H,br), 2.75 (4H,t), 2.9(1H,d), 3.16(1H,d), 5.8(1H,s), 7.5–7.7(2H,m), 7.77–7.85(1H,m), 8.0(2H, d) and 8.4(1H,d).

EXAMPLE 6

The procedure described in Example 1 was repeated using 2-bromo-5-methylpyridine in place of 5-bromo-2-n-butoxypyridine. Purification by flash chromatography on silica gel using 10% methanol in dichloromethane containing 1% ammonia (density, 0.88 g/cm$^3$) as eluent gave 3-[2-(5-methylpyrid-2-yl)ethynyl]quinuclidin-3-ol as a solid, m.p. 176°–180° C.; NMR(DMSOd$_6$): 1.25–1.42(1H, m), 1.55–1.72(1H,m), 1.8–2.0(2H,m), 2.02(1H,br), 2.35 (3H,s), 2.75(4H,t), 2.9(1H,d), 3.16(1H,d), 5.8(1H,s), 7.37 (1H,d), 7.6(1H,d) and 8.4(1H,br).

EXAMPLE 7

The procedure described in Example 1 was repeated using 2-chloro-5-(methoxycarbonyl)pyridine in place of 5-bromo-2-n-butoxypyridine. Purification by flash chromatography on alumina (ICN Biomedicals N32-63) using 2% methanol in dichloromethane as eluent gave 3-[2-(5-methoxycarbonylpyrid-2-yl)ethynyl]quinuclidin-3-ol as a solid, m.p. 180°–182° C., NMR(DMSOd$_6$): 1.25–1.42(1H, m), 1.55–1.72(1H,m), 1.8–2.0(2H,m), 2.02(1H,br), 2.75 (4H,t), 2.9(1H,d), 3.16(1H,d), 3.92(3H,s), 5.8(1H,s), 7.52 (1H,d), 8.28(1H,d of d) and 9.01(1H,d).

EXAMPLE 8

Illustrative pharmaceutical dosage forms suitable for presenting the compounds of the invention for therapeutic or prophylactic use include the following tablet and capsule formulations, which may be obtained by conventional procedures well known in the art of pharmacy and are suitable for therapeutic or prophylactic use in humans:

| (a) Tablet I | mg/tablet |
|---|---|
| Compound Z* | 1.0 |
| Lactose Ph. Eur. | 93.25 |
| Croscarmellose sodium | 4.0 |
| Maize starch paste (5% w/v aqueous paste) | 0.75 |
| Magnesium stearate | 1.0 |

| (b) Tablet II | mg/tablet |
|---|---|
| Compound Z* | 50 |
| Lactose Ph. Eur | 223.75 |
| Croscarmellose sodium | 6.0 |
| Maize starch | 15.0 |
| Polyvinylpyrrolidone (5% w/v aqueous paste) | 2.25 |
| Magnesium stearate | 3.0 |
| (c) Tablet III | mg/tablet |
| Compound Z* | 100 |
| Lactose Ph. Eur. | 182.75 |
| Croscarmellose sodium | 12.0 |
| Maize starch paste (5% w/v aqueous paste) | 2.25 |
| Magnesium stearate | 3.0 |
| (d) Capsule | mg/capsule |
| Compound Z* | 10 |
| Lactose Ph. Eur. | 488.5 |
| Magnesium stearate | 1.5 |

Note
*The active ingredient Compound Z is a compound of formula I, or a salt thereof, for example a compound of formula I described in any of the preceding Examples.

The tablet compostions (a)–(c) may be enteric coated by conventional means, for example, with cellulose acetate phthalate.

SCHEME 1

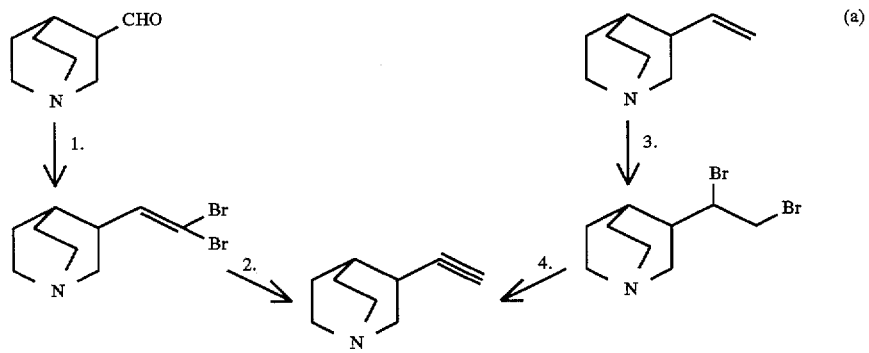

1. CBr$_4$/PPh$_3$/Zn, CH$_2$Cl$_2$, room temperature
2. (a) nBuLi (2 equiv), THF, −60° C., argon atmosphere (b) H$_2$O
3. Br$_2$/H$_2$O
4. t.BuOK, tBuOH, reflux

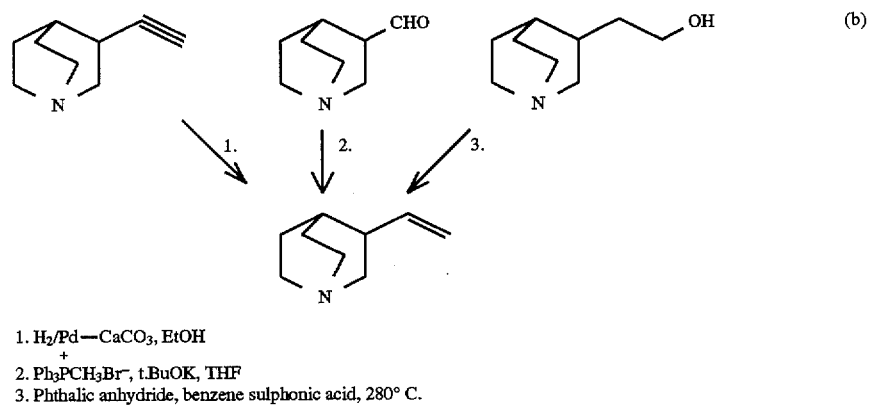

1. H$_2$/Pd—CaCO$_3$, EtOH
   +
2. Ph$_3$PCH$_3$Br$^-$, t.BuOK, THF
3. Phthalic anhydride, benzene sulphonic acid, 280° C.

SCHEME 2

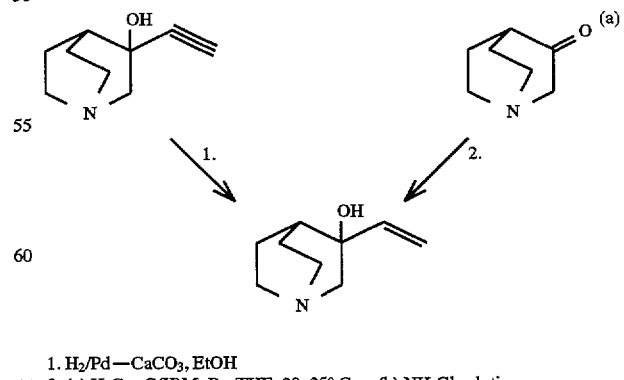

1. H$_2$/Pd—CaCO$_3$, EtOH
2. (a) H$_2$C=C(H)MgBr, THF, 20–25° C.   (b) NH$_4$Cl solution

-continued
SCHEME 2

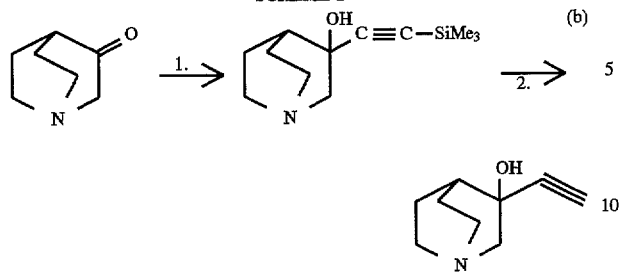

1. Me₃Si—C≡C—Li, THF, -70° C., argon atmosphere
2. K₂CO₃, MeOH, 20-25° C.

CHEMICAL FORMULAE

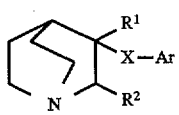 I

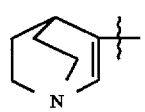 Ia

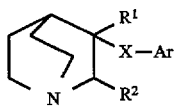 II

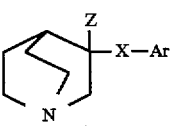 III

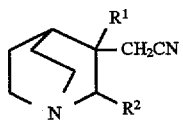 IV

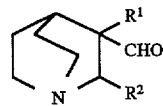 V

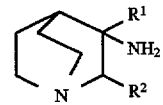 VI

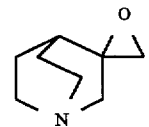 VII

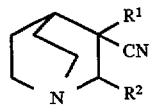 VIII

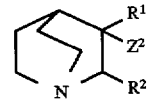 IX

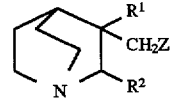

-continued
CHEMICAL FORMULAE

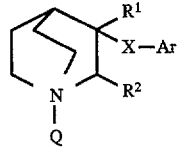 X

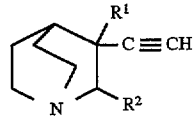 XI

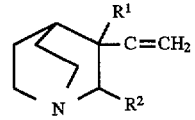 XII

I claim:
1. A compound of formula I:

or a pharmaceutically acceptable salt thereof, wherein:

$R^1$ is hydrogen or hydroxy $R^2$ is hydrogen; or $R^1$ and $R^2$ are joined together so that $CR^1$—$CR^2$ is a double bond;

X is selected from —CH₂CH₂—, —CH=CH—, —C≡C—, —CH₂O—, —OCH₂—, —CH₂CO—, —COCH₂—, —N=CH—, —CH=N—, —CH₂S(O)$_n$— and —S(O)$_n$CH₂—, wherein n is 0, 1 or 2;

Ar is an aromatic 5-membered or 6-membered heterocyclic ring containing from one to three heteroatoms independently selected from nitrogen, oxygen and sulphur, which ring is optionally fused to a benzene ring;

and wherein Ar may optionally be unsubstituted or may bear one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C)alkylsulphonyl, halogeno-(1–6C)alkyl, (1–6C)alkanoylamino, ureido, N'-(1–6C)alkylureido, (1–6C)alkanoyl and oxime derivatives thereof and O-(1–6C)alkyl ethers of said oxime derivatives; provided that when $R^1$ is hydroxy, X is not selected from —OCH₂—, —N=CH— and —S(O)$_n$CH₂—, wherein n is 0, 1 or 2; and that when $R^1$ and $R^2$ are both hydrogen, X is —CH₂O—, —OCH₂—, —CH₂S(O)$_n$— or —S(O)$_n$CH₂—, wherein n is 0, 1 or 2, then Ar is not a 5, 6 or 7 membered heteroaryl moiety.

2. A compound of formula I:

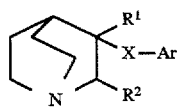

or a pharmaceutically acceptable salt thereof, wherein:

$R^1$ is hydroxy
$R^2$ is hydrogen; or
$R^1$ and $R^2$ are joined together so that $CR^1$—$CR^2$ is a double bond;

X is selected from —$CH_2CH_2$—, —CH=CH—, —C≡C—, —$CH_2O$—, —$OCH_2$—, —$CH_2NH$—, —$NHCH_2$—, —$CH_2CO$—, —$COCH_2$—, —N=CH—, —CH=N—, —$CH_2S(O)_n$— and —$S(O)_nCH_2$—, wherein n is 0, 1 or 2;

Ar is an aromatic 5-membered or 6-membered heterocyclic ring containing from one to three heteroatoms independently selected from nitrogen, oxygen and sulphur, which ring is optionally fused to a benzene ring;

and wherein Ar may optionally be unsubstituted or may bear one or more substituents independently selected from halogeno, hydroxy, amino, nitro, cyano, carboxy, carbamoyl, (1–6C)alkyl, (2–6C)alkenyl, (2–6C) alkynyl, (1–6C)alkoxy, (1–6C) alkylamino, di-[(1–6C)alkyl]amino, N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C) alkylsulphonyl, halogeno-(1–6C)alkyl, (1–6C) alkanoylamino, ureido, N'-(1–6C)alkylureido, (1–6C) alkanoyl and oxime derivatives thereof and O-(1–6C) alkyl ethers of said oxime derivatives; provided that when $R^1$ is hydroxy, X is not selected from —$OCH_2$—, —$NHCH_2$—, —N=CH— and —$S(O)_nCH_2$— wherein n is 0, 1 or 2.

3. A process for preparing a compound of formula I, or a pharmaceutically acceptable salt thereof, as claimed in claim 1 or 2, which process is selected from:

(d) for those compounds of formula I in which X is —$CH_2CO$—, reacting an organometallic compound of formula Ar—M in which M is a metal atom or a derivative thereof, with a compound of formula III;

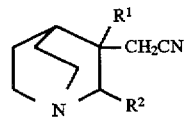

(i) for compounds of formula I in which X is —$COCH_2$—, reacting a compound of formula Ar—$CH_2M$ in which M is a metal atom or a derivative thereof, with a compound of formula VII;

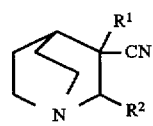

(j) for those compounds of formula I in which X is —$CH_2O$— or —$CH_2S$—, reacting a compound of formula $ArCH_2Z^1$ with a compound of formula VIII, in which $Z^1$ is a leaving group and $Z^2$ is —YM, or $Z^1$ is —YM and $Z^2$ is a leaving group, and wherein Y is oxygen or sulphur (as appropriate) and M is a metal atom;

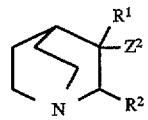

(n) for those compounds of formula I in which $R^1$ is hydroxy, $R^2$ is hydrogen and X ix —C≡C—, reacting a compound of formula Ar—C≡C—M in which M is a metal atom, with quinuclidin-3-one;

(o) for those compounds in which $R^1$ and $R^2$ are hydrogen and X is —C≡C—, reacting a compound of formula Ar—C≡C—M in which M is a metal atom with a compound of formula VIII in which Z is a leaving group;

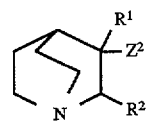

(p) for those compounds in which X is —C≡C—, and $R^1$ is hydrogen or hydroxy and $R^2$ is hydrogen, reacting a compound of formula XI with a compound of formula Ar—Z in which Z is a leaving group in the presence of a catalyst;

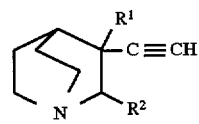

(q) for those compounds in which X is —CH=CH— and $R^1$ is hydrogen or hydroxy and $R^2$ is hydrogen, reacting a compound of formula XII with a compound of formula Ar—Z in which Z is a leaving group in the presence of a catalyst;

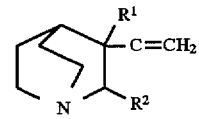

and whereafter, when a pharmaceutically acceptable salt is required, treating the compound of formula I with an acid which affords a physiologically acceptable anion or a base which affords a physiologically acceptable cation.

4. A method of inhibiting squalene synthase in a warm-blooded animal (such as man) requiring such treatment, which method comprises administering to said animal an effective amount of a compound of formula I:

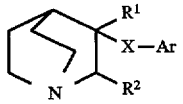

or a pharmaceutically-acceptable salt thereof wherein:

$R^1$ is hydrogen or hydroxy
$R^2$ is hydrogen; or
$R^1$ and $R^2$ are joined together so that $CR^1$—$CR^2$ is a double bond;

X is selected from —$CH_2CH_2$—, —CH=CH—, —C≡C—, —$CH_2O$—, —$OCH_2$—, —$CH_2NH$—, —CH=N—, —N=CH—, —$NHCH_2$—, —$CH_2CO$—, —$COCH_2$—, —$CH_2S(O)_n$— and —$S(O)_nCH_2$—, wherein n is 0, 1 or 2;

Ar is a heterocyclic moiety containing from one to three heteroatoms independently selected from nitrogen, oxygen and sulphur;

and wherein Ar may optionally be unsubstituted or may bear one or more substituents independently selected from halogeno, hydroxy, amino, nitro, cyano, carboxy, carbamoyl, (1–6C)alkyl, (2–6C) alkenyl, (2–6C) alkynyl, (1–6C) alkoxy, (1–6C) alkylamino, di-[(1–6C)alkyl]amino, N-(1–6C)alkylcarbamoyl, di-N,N-[(1–6C) alkyl]carbamoyl, (1–6C) alkoxycarbonyl, (1–6C) alkylthio, (1–6C) alkylsulphinyl, (1–6C) alkylsulphonyl, halogeno-(1–6C) alkyl, (1–6C) alkanoylamino, (1–6C) alkanoyl and oxime derivatives thereof and O-(1–6C)alkyl ethers of said oxime derivatives;

provided that when $R^1$ is hydroxy, X is not selected from —OCH$_2$—, —NHCH$_2$—, —N=CH— and —SCH$_2$—.

5. A method of treating cholesterol biosynthesis in a warm-blooded animal requiring such treatment, which method comprises administering to said animal an effective amount of a compound of formula I,

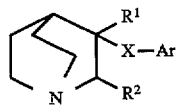

or a pharmaceutically-acceptable salt thereof wherein:
$R^1$ is hydrogen or hydroxy
$R^2$ is hydrogen; or
or $R^1$ and $R^2$ are joined together so that $CR^1$—$CR^2$ is a double bond;
X is selected from —CH$_2$CH$_2$—, —CH=CH—, —C≡C—, —CH$_2$O—, —OCH$_2$—, —CH$_2$NH—, —CH=N—, —N=CH—, —NHCH$_2$—, —CH$_2$CO—, —COCH$_2$—, —CH$_2$S(O)$_n$— and —S(O)$_n$CH$_2$—, wherein n is 0, 1 or 2;
Ar is a heterocyclic moiety containing from one to three heteroatoms independently selected from nitrogen, oxygen and sulphur;
and wherein Ar may optionally be unsubstituted or may bear one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, di-N,N-[(1–6C)alkyl]carbamoyl, (1–6C)alkoxycarbonyl, (1–6C)alkylthio, (1–6C) alkylsulphinyl, (1–6C)alkylsulphonyl, halogeno-(1–6C) alkyl, (1–6C)alkanoylamino, (1–6C)alkanoyl and oxime derivatives thereof and O-(1–6C)alkyl ethers of said oxime derivatives;
provided that when $R^1$ is hydroxy, X is not selected from —OCH$_2$—, —NHCH$_2$—, —N=CH— and —SCH$_2$—.

6. A method of treating hypercholesterolemia or atherosclerosis in a warm-blooded animal comprising administering to said animal an effective amount of a compound of formula I,

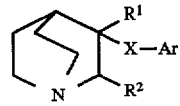

or a pharmaceutically-acceptable salt thereof wherein:
$R^1$ is hydrogen or hydroxy
$R^2$ is hydrogen; or
or $R^1$ and $R^2$ are joined together so that $CR^1$—$CR^2$ is a double bond;
X is selected from —CH$_2$CH$_2$—, —CH=CH—, —C≡C—, —CH$_2$—O, —OCH$_2$—, —CH$_2$NH—, —CH=N—, —N=CH—, —NHCH$_2$—, —CH$_2$CO—, —COCH$_2$—, —CH$_2$S(O)$_n$— and —S(O)$_n$CH$_2$—, wherein n is 0, 1 or 2;

Ar is a heterocyclic moiety containing from one to three heteroatoms independently selected from nitrogen, oxygen and sulphur;

and wherein Ar may optionally be unsubstituted or may bear one or more substituents independently selected from halogeno, hydroxy, amino, nitro, cyano, carboxy, carbamoyl, (1–6C)alkyl, (2–6C)alkenyl, (2–6C) alkynyl, (1–6C)alkoxy, (1–6C)alkylamino, di-[(1–6C) alkyl]amino, N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C) alkylsulphonyl, halogeno-(1–6C)alkyl, (1–6C) alkanoylamino, (1–6C)alkanoyl and oxime derivatives thereof and O-(1–6C)alkyl ethers of said oxime derivatives;

provided that when $R^1$ is hydroxy, X is not selected from —OCH$_2$—, —NHCH$_2$—, —N=CH— and —SCH$_2$—.

7. A compound as claimed in claim 1 or 2 wherein X is selected from —CH$_2$CH$_2$—, —CH=CH—, —C≡C— —N=CH—, —CH=N—, —CH$_2$S(O)$_n$— and —S(O)$_n$CH$_2$—, wherein n is 0, 1 or 2.

8. A compound as claimed in claim 1 or 2 wherein Ar is selected from furyl, pyrrolyl, thienyl, pyridyl, pyrazinyl, pyrimidinyl, pyridazinyl, imidazolyl, oxazolyl, isooxazolyl, thiazolyl, isothiazolyl, oxadiazolyl, 1,2,3-triazolyl, 1,2,4-triazolyl, benzfuranyl, quinolyl, isoquinolyl, benzimidazolyl, and indolyl.

9. A compound as claimed in claim 1 or 2 wherein Ar is selected from pyridyl and quinolyl.

10. A compound as claimed in claim 5 wherein Ar is selected from 6-butoxypyrid-3-yl, 3-pyridyl, 5-bromopyrid-2-yl, 3-quinolyl, 2-quinoyl, 5-methylpyrid-2-yl and 5-methoxycarbonylpyrid-2-yl.

11. A compound as claimed in claim 1 or 2 wherein X is —C≡C—.

12. A compound as claimed in claim 1 or 2 wherein Ar may optionally be unsubstituted or may bear one or more substituents independently selected from halogeno, hydroxy, nitro, (1–6C)alkyl, (2–6C)alkenyl, (1–6C)alkoxy, (1–6C) alkanoylamimo, halogeno(1–6C)alkyl, (1–6C)alkanoyl and oxime derivatives thereof and O(1–6C)alkyl ethers of said oximes.

13. A compound which is selected from:
3-[2-(6-butoxypyrid-3-yl)ethynyl]quinuclidin-3-ol;
3-[2-(3-pyridyl)ethynyl]quinuclidin-3-ol;
3-[2-(6-bromopyrid-3-yl)ethynyl]quinuclidin-3-ol;
3-[2-(3-quinolyl)ethynyl]quinuclidin-3-ol;
3-[2-(2-quinolyl)ethynyl]quinuclidin-3-ol;
3-[2-(5-methylpyrid-2-yl)ethynyl]quinuclidin-3-ol;
3-[2-(5-methoxycarbonylpyrid-2-yl)ethynyl]quinuclidin-3-ol;

and their pharmaceutically acceptable salts.

14. A pharmaceutical composition comprising a compound of formula I, or a pharmaceutically acceptable salt thereof thereof, as claimed in claim 1 or 2 together with a pharmaceutically acceptable diluent or carrier.

* * * * *